US00RE37958E

(19) United States
(12) Reissued Patent
Foster et al.

(10) Patent Number: US RE37,958 E
(45) Date of Reissued Patent: Jan. 7, 2003

(54) DNA SEQUENCE CODING FOR PROTEIN C

(75) Inventors: Donald C. Foster, Seattle, WA (US); Earl W. Davie, Bellevue, WA (US)

(73) Assignee: Board of Regents of the University of Washington, Seattle, WA (US)

(21) Appl. No.: 09/882,150

(22) Filed: Jun. 15, 2001

Related U.S. Patent Documents

Reissue of:
(64) Patent No.: 4,968,626
Issued: Nov. 6, 1990
Appl. No.: 06/766,109
Filed: Aug. 15, 1985

(51) Int. Cl.[7] ..... C12N 15/00; C12N 9/64; C07H 15/12

(52) U.S. Cl. ..... 435/320.1; 435/226; 435/69.1; 435/440; 435/252.33; 536/23.2

(58) Field of Search ..... 435/320.1, 226, 435/69.1, 440, 252.33; 536/23.2

(56) References Cited

U.S. PATENT DOCUMENTS 4,775,624 A * 10/1988 Bang et al.
4,784,950 A * 11/1988 Hagen et al.

FOREIGN PATENT DOCUMENTS

EP 138222 * 4/1985
GB WO85/00521 * 2/1985

OTHER PUBLICATIONS

Stenflo et al., (1982), Journal of Biochemistry, vol. 257, pp. 12180–12190.*
Ferlund et al., (1982), Journal of Biochemistry, vol. 257, pp. 12170–12179.*
Beckmann et al., (Jul. 25, 1985), Nucleic Acids Research, vol. 13, pp. 6233–6247.*
Foster and Davie, (1984), Proceedings National Academy Sciences, U.S.A., vol. 81, pp. 4766–4770.*
Foster et al., (1985), Proceedings National Academy Science, U.S.A., vol. 82, pp. 4673–4677.*
Degan et al., (1983), Biochemistry, vol. 22, pp. 2087–2092.*
Long, G., et al., Sep. 1984, PNAS, 81:5653–5656.*
Kaufman and Sharp, Mol. and Cell. Biol., 2:1304–1319, 1982.*
Kaufman, Proc. Natl. Acad. Sci., (U.S.A.), 82:689–693, 1985.*
Hermonat et al., Proc. Natl. Acad. Sci., (U.S.A.), 81:6466–6740, 1984.*
Esmon et al., Proc. Natl. Acad. Sci., (U.S.A.), 78:2249–2252, 1981.*
Ginsburg et al., Science, 228:1401–1406, 1985.*
Katayama et al., Proc. Natl. Acad. Sci., (U.S.A.), 76:4990–4994, 1979.*
Kisiel et al., Biochem., 16:5824–5831, 1977.*
Long et al., Proc. Natl. Acad. Sci., (U.S.A.), 81:5653–5656, 1984.*
Walker et al., Biochim. et Biophys. Acta, 571:333–342, 1979.*
McMullen et al., Biochem. and Biophys. Res. Comm., 115:8–14, 1983.*
Beckmann et al., Fed. Proc., 44:1069, 1985.*
W. Kisiel et al., "Protein C", Methods of Enzymology, 80:320–332, 1981.*
J. H. Griffin et al., "Deficiency of Protein C in Congential Thrombotic Disease", J. Clin. Invest., 68:1370–1373, 1981.*
Walter Kisiel, "Human Plamsa Protein C", J. Clin Invest., 64:761–769, 1979.*
V. W. M. van Hinsbergh et al., "Activated Protein C Decreases Plasminogen Activator–Inhibitor Activity in Endothelial Cell–Conditioned Medium", Blood 65:444–451, Feb. 1985.*
W. Kisiel et al., "Enzymological Aspects of Blood Coagulation", Behring Inst. Mitt., 73:29–42, 1983.*
J. E. Gardiner and J. H. Griffin, "Human Protein C and Thromboembolic Disease", Progress in Hematology, pp. 265–278, 1983.*
Philip C. Comp et al., "Generation of Fibrinolytic Activity by Infusion of Activated Protein C into Dogs", J. Clin. Invest., 68:1221–1228, 1981.*
Y. Sakata et al., "Activated Protein C Stimulates the Fibrinolytic Activity of Cultured Endothelial Cells and Decreases Antiactivator Activity", Proc. Natl. Acad. Sci. U.S.A., 82:1121–1125, 1985.*
A. Broekmans et al., "Congential Protein C Deficiency and Venous Thromboembolism", The New England Journal of Medicine, 309:340–344, 1983.*
U. Seligsohn et al., "Homozygous Protein C Deficiency Manifested by Massive Venous Thrombosis in the Newborn", The New England Journal of Medicine, 310:559–562, 1984.*
R. A. Marlar, "Mechanism of Action of Human Activated Protein C, a Thrombin–Dependent Anticoagulant Enzyme", Blood, 59:1067–1072, 1982.*

* cited by examiner

*Primary Examiner*—James Ketter

(57) ABSTRACT

Genomic and cDNA sequences coding for a protein having substantially the same biological activity as human protein C are disclosed. Recombinant plasmids and bacteriophage transfer vectors incorporating these sequences are also disclosed.

3 Claims, 9 Drawing Sheets

```
GGCCTAAAAC CACACAGGCC TGGCCTTGAG TCCTGGCTCT GCGAGTAATG CATGGATGTA AACATGGAGA CCCAGGACCT TGCCTCAGTC TTCCGAGTCT GGTGCCTGCA GTGTACTGAT GGTGTGAGAC  -831
CCTACTCCTG GAGGATGGGG GACAGAATCT GATCGATCCC CTGGGTTGGT GACTTCCCTG TGCAATCAAC GGAGACCAGC AAGGGTTGGA TTTTTAATAA ACCACTTAAC TCCTCCGAGT CTCAGTTTCC  -701
CCCTCTATGA AATGGGGTTG ACAGCATTAA TAACTACCTC TTGGGTGGTT GTGAGCCTTA ACTGAAGTCA TAATATCTCA TGTTTACTGA GCATGAGCTA TGTGCAAAGC CTGTTTTGAG AGCTTTATGT  -571
GGACTAACTC CTTTAATTCT CACAACACCC TTTAAGGCAC AGATACACCA CGTTATTCCA TCCATTTTAC AAATGAGGAA ACTGAGGCAT GGAGCAGTTA AGCATCTTGC CCAACATTGC CCTCCAGTAA  -441
GTGCTGGAGC TGGAATTTGC ACCGTGCAGT CTGGCTTCAT GGCCTGCCCT GTGAATCCTG TAAAAATTGT TTGAAAGACA CCATGAGTGT CCAATCAACG TTAGCTAATA TTCTCAGCCC AGTCATCAGA  -311
CCGGCAGAGG CACCCACCCC ACTGTCCCCA GGGAGGACAC AAACATCCTG GCACCCTCTC CACTGCATTC TGGAGCTGCT TTCTAGGCAG GCAGTGTGAG CTCAGCCCCA CGTAGAGCGG GCAGCCGAGG  -181
CCTTCTGAGG CTATGTCTCT AGCGAACAAG GACCCTCAAT TCCAGCTTCC GCCTGACGGC CAGCACACAG GGACAGCCCT TTCATTCCGC TTCCACCTGG GGGTGCAGGC AGAGCAGCAG CGGGGGTAGC  -51
                                                        -42
                                                        Met Trp Gln Leu Thr Ser Leu Leu Leu Phe Val Ala Thr Trp Gly Ile Ser Gly Thr Pro Ala
ACTGCCCGGA GCTCAGAAGT CCTCCTCAGA CAGGTGCCAG TGCCTCCAGA ATG TGG CAG CTC ACA AGC CTC CTG CTG TTC GTG GCC ACC TGG GGA ATT TCC GGC ACA CCA GCT  63
    -20
Pro Leu
CCT CTT G GTAAGGCCAC CCCACCCCTA CCCCGGGACC CTTGTGGCCT CTACAAGGCC CTGGTGGCAT CTGCCCAGGC CTTCACAGCT TCCACCATCT CTCTGAGCCC TGGGTGAGGT GAGGGGCAGA  190

TGGGAATGGC AGGAATCAAC TGACAAGTCC CAGGTAGGCC AGCTGCCAGA GTGCCACACA GGGGCTGCCA GGGCAGGCAT GCGTGATGGC AGGGAGCCCC GCGATGACCT CCTAAAGCTC CCTCCTCCAC  320
ACGGGGATGG TCACAGAGTC CCCTGGGCCT TCCCTCTCCA CCCACTCACT CCCTCAACTG TGAAGACCCC AGGCCCAGGC TACCGTCCAC ACTATCCAGC ACAGCCTCCC CTACTCAAAT GCACACTGGC  450
CTCATGGCTG CCCTGCCCCA ACCCCTTTCC TGGTCTCCAC AGCCAACGGG AGGAGGCCAT GATTCTTGGG GAGGTCCGCA GGCACATGGG CCCCTAAAGC CACACCAGGC TGTTGGTTTC ATTTGTGCCT  580
TTATAGAGCT GTTTATCTGC TTGGGACCTG CACCTCCACC CTTTCCCAAG GTGCCCTCAG CTCAGGCATA CCCTCCTCTA GGATGCCTTT TCCCCCATCC CTTCTTGCTC ACACCCCCAA CTTGATCTCT  710
CCCTCCTAAC TGTGCCCTGC ACCAAGACAG ACACTTCACA GAGCCCAGGA CACACCTGGG GACCCTTCCT GGGTGATAGG TCTGTCTATC CTCCAGGTGT CCCTGCCCAA GGGGAGAAGC ATGGGGAATA  840
CTTGGTTGGG GGAGGAAAGG AAGACTGGGG GGATGTGTCA AGATGGGGCT GCATGTGGTG TACTGGCAGA AGAGTGAGAG GATTTAACTT GGCAGCCTTT ACAGCAGCAG CCAGGGCTTG AGTACTTATC  970
TCTGGGCCAG GCTGTATTGG ATGTTTTACA TGACGGTCTC ATCCCCATGT TTTTGGATGA GTAAATTGAA CCTTAGAAAG GTAAAGACAC TGGCTCAAGG TCACACAGAG ATCGGGGTGG GGTTCACAGG 1100
GAGGCCTGTC CATCTCAGAG CAAGGCTTCG TCCTCCAACT GCCATCTGCT TCCTGGGGAG GAAAAGAGCA GAGGACCCCT GCGCCAAGCC ATGACCTAGA ATTAGAATGA GTCTTGAGGG GGCGGAGACA 1230
                                                                                                                                -19
                                                                                                                                Asp Ser Val Phe Ser Ser Ser
AGACCTTCCC AGGCTCTCCC AGCTCTGCTT CCTCAGACCC CCTCATGGCC CCAGCCCCTC TTAGGCCCCT CACCAAGGTG AGCTCCCCTC CCTCCAAAAC CAGT AC TCA GTG TTC TCC AGC AGC  1353
                                                -1  +1
Glu Arg Ala His Gln Val Leu Arg Ile Arg Lys Arg Ala Asn Ser Phe Leu Glu Glu Leu Arg His Ser Ser Leu Glu Arg Glu Cys Ile Glu Glu Ile Cys Asp
GAG CGT GCC CAC CAG GTG CTG CGG ATC CGC AAA CGT GCC AAC TCC TTC CTG GAG GAG CTC CGT CAC AGC AGC CTG GAG CGG GAG TGC ATA GAG GAG ATC TGT GAC  1458
                                                                    37
        Phe Glu Glu Ala Lys Glu Ile Phe Gln Asn Val Asp Asp Thr
        TTC GAG GAG GCC AAG GAA ATT TTC CAA AAT GTG GAT GAC ACA GTAAGGCCAC CATGGGTCCA GAGGATGAGG CTCAGGGGCG AGCTGGTAAC CAGCAGGGGC CTCGAGGAGC  1570
```

FIG. 2A

```
AGGTGGGGAC TCAATGCTGA GGCCCTCTTA GGAGTTGTGG GGGTGGCTGA GTGGAGCGAT TAGGATGCTG GCCCTATGAT GTCGGCCAGG CACATGTGAC TGCAAGAAAC AGAATTCAGG AAGAAGCTCC   1700
AGGAAAGAGT GTGGGGTGAC CCTAGGTGGG GACTCCCACA GCCACAGTGT AGGTGGTTCA GTCCACCCTC CAGCCACTGC TGAGCACCAC TGCCTCCCCG TCCCACCTCA CAAAGAGGGG ACCTAAAGAC   1830
CACCCTGCTT CCACCCATGC CTCTGCTGAT CAGGGTGTGT GTGTGACCGA AACTCACTTC TGTCCACATA AAATCGCTCA CTCTGTGCCT CACATCAAAG GGAGAAAATC TGATTGTTCA GGGGGTCGGA   1960
AGACAGGGTC TGTGTCCTAT TTGTCTAAGG GTCAGAGTCC TTTGGAGCCC CCAGAGTCCT GTGGACGTGG CCCTAGGTAG TAGGGTGAGC TTGGTAACGG GGCTGGCTTC CTGAGACAAG GCTCAGACCC   2090
GCTCTGTCCC TGGGGATCGC TTCAGCCACC AGGACCTGAA AATTGTGCAC GCCTGGGCCC CCTTCCAACG CATCCAGGGA TGCTTTCCAG TGGAGGCTTT CAGGGCAGGA GACCCTCTGG CCTGCACCCT   2220
CTCTTGCCCT CAGCCTCCAC CTCCTTGACT GGACCCCCAT CTGGACCTCC ATCCCCACCA CCTCTTTCCC CAGTGGCCTC CCTGGCAGAC ACCACAGTGA CTTTCTGCAG GCACATATCT GATCACATCA   2350
AGTCCCCACC GTGCTCCCAC CTCACCCATG GTCTCTCAGC CCCAGCAGCC TTGGCTGGCC TCTCTGATGG AGCAGGCATC AGGCACAGGC CGTGGGTCTC AACGTGGGCT GGGTGGTCCT GGACCAGCAG   2480
CAGCCGCCGC AGCAGCAACC CTGGTACCTG GTTAGGAACG CAGACCCTCT GCCCCCATCC TCCCAACTCT GAAAAACACT GGCTTAGGGA AAGGCGCGAT GCTCAGGGGT CCCCCAAAGC CCGCAGGCAG   2610
AGGGAGTGAT GGGACTGGAA GGAGGCCGAG TGACTTGGTG AGGGATTCGG GTCCCTTGCA TGCAGAGGCT GCTGTGGGAG CGGACAGTCG CGAGAGCAGC ACTGCAGCTG CATGGGGAGA GGGTGTTGCT   2740
CCAGGGACGT GGGATGGAGG CTGGGCGCGG GCGGGTGGCG CTGGAGGGCG GGGGAGGGGC AGGGAGCACC AGCTCCTAGC AGCCAACGAC CATCGGGCGT CGATCCCTGT TTGTCTGGAA GCCCTCCCCT   2870
                                                                                                                                  38                                                                  45
                                                                                                                                  Leu Ala Phe Trp Ser Lys His Val
CCCCTGCCCG CTCACCCGCT GCCCTGCCCC ACCCGGGCGC GCCCCTCCGC ACACCGGCTG CAGGAGCCTG ACGCTGCCCG CTCTCTCCGC AGTCTG GCC TTC TGG TCC AAG CAC GTC GTGTGAGT   2993
                                                                                                                                  46
                                                                                                                                  Asp Gly Asp Gln Cys Leu Val Leu Pro Leu Glu
GCGTTCTAGA TCCCCGGCTG GACTACCGGC GCCCGCGCCC CTCGGGATCT CTGGCCGCTG ACCCCCTACC CCGCCTTGTG TCGCAGT AC GGT GAC CAG TGC TTG GTC TTG CCC TTG GAG   3111
                                                                                                                                                                                                                                  91
His Pro Cys Ala Ser Leu Cys Cys Gly His Gly Thr Cys Ile Asp Gly Ile Gly Ser Phe Ser Cys Asp Cys Arg Ser Gly Trp Glu Gly Arg Phe Cys Gln Arg
CAC CCG TGC GCC AGC CTG TGC TGC GGG CAC GGC ACG TGC ATC GAC GGC ATC GGC AGC TTC AGC TGC GAC TGC CGC AGC GGC TGG GAG GGC CGC TTC TGC CAG CGC   3216
                                                                                                                                  92                                                                  ◆
                                                                                                                                  Glu Val Ser Phe Leu Asn
G GTGAGGG GGAGAGGTGG ATGCTGGCGG GCGGCGGGGC GGGGCTGGGG CCGGGTTGGG GGCGCGGCAC CAGCACCAGC TGCCCGCGCC CTCCCCTGCC CGCAGT AG GTG AGC TTC CTC AAT   3336

Cys Ser Leu Asp Asn Gly Gly Cys Thr His Tyr Cys Leu Glu Glu Val Gly Trp Arg Arg Cys Ser Cys Ala Pro Gly Tyr Lys Leu Gly Asp Asp Leu Leu Gln
TGC TCT CTG GAC AAC GGC GGC TGC ACG CAT TAC TGC CTA GAG GAG GTG GGC TGG CGG CGC TGT AGC TGT GCG CCT GGC TAC AAG CTG GGG GAC GAC CTC CTG CAG   3440
                136
  Cys His Pro Ala
  TGT CAC CCC GCA G GTGAGAAGCC CCCAATACAT CGCCCAGGAA TCACGCTGGG TGCGGGGTGG GCAGGCCCCT GACGGGCGCG GCGCGGGGGG CTCAGGAGGG TTTCTAGGGA GGGAGCGAGG   3564
AACAGAGTTG AGCCTTGGGG CAGCGGCAGA CGCGCCCAAC ACCGGGGCCA CTGTTAGCGC AATCAGCCCG GGAGCTGGGC GCGCCCTCCG CTTTCCCTGC TTCCTTTCTT CCTGGCGTCC CCGCTTCCTC   3694
CGGGCGCCCC TGCGACCTGG GGCCACCTCC TGGAGCGCAA GCCCAGTGGT GGCTCCGCTC CCCAGTCTGA GCGTATCTGG GGCGAGGCGT GCAGCGTCCT CCTCCATGTA GCCTGGCTGC GTTTTTCTCT   3824
GACGTTGTCC GGCGTGCATC GCATTTCCCT CTTTACCCCC TTGCTTCCTT GAGGAGAGAA CAGAATCCCG ATTCTGCCTT CTTCTATATT TTCCTTTTTA TGCATTTTAA TCAAATTTAT ATATGTATGA   3954
AACTTTAAAA ATCAGAGTTT TACAACTCTT ACACTTTCAG CATGCTGTTC CTTGGCATGG GTCCTTTTTT CATTCATTTT CATAAAAGGT GGACCCTTTT AATGTGGAAA TTCCTATCTT CTGCCTCTAG   4084
GGCATTTATC ACTTATTTCT TCTACAATCT CCCCTTTACT TCCTCTATTT TCTCTTTCTG GACCTCCCAT TATTCAGACC TCTTTCCTCT AGTTTTATTG TCTCTTCTAT TTCCCATCTC TTTGACTTTG   4214
TGTTTTCTTT CAGGGAACTT TCTTTTTTTT CTTTTTTTTT GAGATGGAGT TTCACTCTTG TTGTCCCAGG CTGGAGTGCA ATGACGTGAT CTCAGCTCAC CACAACCTCC GCCTCCTGGA TTCAAGCGAT   4344
TCTCCTGCCG CAGCCTCCCG AGTAGCTGGG ATTACAGGCA TGCGCCACCA CGCCCAGCTA ATTTTGTGTT TTTAGTAGAG AAGGGGTTTC TCCGTGTTGG TCAAGCTGGT CTTGAACTCC TGACCTCAGG   4474
TGATCCACCT GCCTTGGCCT CCTAAAGTGC TGGGATTACA GGCGTGAGCC ACCGCGCCCA GCCTCTTTCA GGGAACTTTC TACAACTTTA TAATTCAATT CTTCTGCAGA AAAAAATTTT TGGCCAGGCT   4604
CAGTAGCTCA GACCAATAAT TCCAGCACTT TGAGAGGCTG AGGTGGGAGG ATTGCTTGAG CTTGGGAGTT TGAGACTAGC CTGGGCAACA CAGTGAGACC CTGTCTCTAT TTTTAAAAAA AGTAAAAAAA   4734
GATCTAAAAA TTTAACTTTT TATTTTGAAA TAATTAGATA TTTCCAGGAA GCTGCAAAGA AATGCCTGGT GGGCCTGTTG GCTGTGGGTT TCCTGCAAGG CCGTGGGAAG GCCCTGTCAT TGGCAGAACC   4864
CCAGATCGTG AGGGCTTTCC TTTTAGGCTG CTTTCTAAGA GGACTCCTCC AAGCTCTTGG AGGATGGAAG ACGCTCACCC ATGGTGTTCG GCCCCTCAGA GCAGGGTGGG GCAGGGGAGC TGGTGCCTGT   4994
GCAGGCTGTG GACATTTGCA TGACTCCCTG TGGTCAGCTA AGAGCACCAC TCCTTCCTGA AGCGGGGCCT GAAGTCCCTA GTCAGAGCCT CTGGTTCACC TTCTGCAGGC AGGGAGAGGG GAGTCAAGTC   5124
AGTGAGGAGG GCTTTCGCAG TTTCTCTTAC AAACTCTCAA CATGCCCTCC CACCTGCACT GCCTTCCTGG AAGCCCCACA GCCTCCTATG GTTCCGTGGT CCAGTCCTTC AGCTTCTGGG CGCCCCCATC   5254
ACGGGCTGAG ATTTTTGCTT TCCAGTCTGC CAAGTCAGTT ACTGTGTCCA TCCATCTGCT GTCAGCTTCT GGAATTGTTG CTGTTGTGCC CTTTCCATTC TTTTGTTATG ATGCAGCTCC CCTGCTGACG   5384
ACGTCCCATT GCTCTTTTAA GTCTAGATAT CTGGACTGGG CATTCAAGGC CCATTTTGAG CAGAGTCGGG CTGACCTTTC AGCCCTCAGT TCTCCATGGA GTATGCGCTC TCTTCTTGGC AGGGAGGCCT   5514
```

FIG. 2B

```
CACAAACATG CCATGCCTAT TGTAGGAGCT CTCCAAGAAT GCTCACCTCC TTCTCCCTGT AATTCCTTTC CTCTGTGAGG AGCTCAGCAG CATCCCATTA TGAGACCTTA CTAATCCCAG GGATCACCCC  5644
CAACAGCCCT GGGGTACAAT GAGCTTTTAA GAAGTTTAAC CACCTATGTA AGGAGACACA GGCAGTGGGC GATGCTGCCT GGCCTGACTC TTGCCATTGG GTGGTACTGT TTGTTGACTG ACTGACTGAC  5774
TGACTGGAGG GGGTTTGTAA TTTGTATCTC AGGGATTACC CCCAACAGCC CTGGGGTACA ATGAGCCTTC AACAAGTTTA ACAACCTATG TAAGGACACA CAGCCAGTGG GTGATGCTGC CTGGTCTGAC  5904
TCTTGCCATT CAGTGGCACT GTTTGTTGAC TGACTGACTG ACTGACTGGC TGACTGGAGG GGGTTCATAG CTAATATTAA TGGAGTGGTC TAAGTATCAT TGGTTCCTTG AACCCTGCAC TGTGGCAAAG  6034
                                                                                                                                  137
                                                                                                                                 Val Lys Phe Pro Cys Gly Arg Pro Trp Lys Arg
TGGCCCACAG GCTGGAGGAG GACCAAGACA GGAGGGCAGT CTCGGGAGGA GTGCCTGGCA GGCCCCTCAC CACCTCTGCC TACCTCAG TG AAG TTC CCT TGT GGG AGG CCC TGG AAG CGG  6154

Met Glu Lys Lys Arg Ser His Leu Lys Arg Asp Thr Glu Asp Gln Glu Asp Gln Val Asp Pro Arg Leu Ile Asp Gly Lys Met Thr Arg Arg Gly Asp Ser Pro
ATG GAG AAG AAG CGC AGT CAC CTG AAA CGA GAC ACA GAA GAC CAA GAA GAC CAA GTA GAT CCG CGG CTC ATT GAT GGG AAG ATG ACC AGG CGG GGA GAC AGC CCC  6259
     184
  Trp Gln
  TGG CAG GTGGGAGGCG AGGCAGCACC GGCTCGTCAC GTGCTGGGTC CGGGATCACT GAGTCCATCC TGGCAGCTAT GCTCAGGGTG CAGAAACCGA GAGGGAAGCG CTGCCATTGC GTTTGGGGGA  6385
TGATGAAGGT GGGGGATGCT TCAGGGAAAG ATGGACGCAA CCTGAGGGGA GAGGAGCAGC CAGGGTGGGT GAGGGGAGGG GCATGGGGGC ATGGAGGGGT CTGCAGGAGG GAGGGTTACA GTTTCTAAAA  6515
AGAGCTGGAA AGACACTGCT CTGCTGGCGG GATTTTAGGC AGAAGCCCTG CTGATGGGAG AGGGCTAGGA GGGAGGGCCG GGCCTGAGTA CCCCTCCAGC CTCCACATGG GAACTGACAC TTACTGGGTT  6645
CCCCTCTCTG CCAGGCATGG GGGAGATAGG AACCAACAAG TGGGAGTATT TGCCCTGGGG ACTCAGACTC TGCAAGGGTC AGGACCCCAA AGACCCGGCA GCCCAGTGGG ACCACAGCCA GGACGGCCCT  6775
TCAAGATAGG GGCTGAGGGA GGCCAAGGGG AACATCCAGG CAGCCTGGGG GCCACAAAGT CTTCCTGGAA GACACAAGGC CTGCCAAGCC TCTAAGGATG AGAGGAGCTC GCTGGGCGAT GTTGGTGTGG  6905
CTGAGGGTGA CTGAAACAGT ATGAACAGTG CAGGAACAGC ATGGGCAAAG GCAGGAAGAC ACCCTGGGAC AGGCTGACAC TGTAAAATGG GCAAAAATAG AAAACGCCAG AAAGGCCTAA GCCTATGCCC  7035
                                                                                                                                  185
                                                                                                                                 Val Val Leu Leu Asp Ser Lys
ATATGACCAG GGAACCCAGG AAAGTGCATA TGAAACCCAG GTGCCCTGGA CTGGAGGCTG TCAGGAGGCA GCCCTGTGAT GTCATCATCC CACCCCATTC CAG GTG GTC CTG CTG GAC TCA AAG  7159
                                                                                O                                                 223
Lys Lys Leu Ala Cys Gly Ala Val Leu Ile His Pro Ser Trp Val Leu Thr Ala Ala His Cys Met Asp Glu Ser Lys Lys Leu Leu Val Arg Leu
AAG AAG CTG GCC TGC GGG GCA GTG CTC ATC CAC CCC TCC TGG GTG CTG ACA GCG GCC CAC TGC ATG GAT GAG TCC AAG AAG CTC CTT GTC AGG CTT G GTATGGGCTG  7266
GAGCCAGGCA GAAGGGGGCT GCCAGAGGCC TGGGTAGGGG GACCAGGCAG GCTGTTCAGG TTTGGGGGAC CCCGCTCCCC AGGTGCTTAA GCAAGAGGCT TCTTGAGCTC CACAGAAGGT GTTTGGGGGG  7396

AAGAGGCCTA TGTGCCCCCA CCCTGCCCAC CCATGTACAC CCAGTATTTT GCAGTAGGGG GTTCTCTGGT GCCCTCTTCG AATCTGGGCA CAGGTACCTG CACACACATG TTTGTGAGGG GCTACACAGA  7526
CCTTCACCTC TCCACTCCCA CTCATGAGGA GCAGGCTGTG TGGGCCTCAG CACCCTTGGG TGCAGAGACC AGCAAGGCCT GGCCTCAGGG CTGTGCCTCC CACAGACTGA CAGGGATGGA GCTGTACAGA  7656
GGGAGCCCTA GCATCTGCCA AAGCCACAAG CTGCTTCCCT AGCAGGCTGG GGGCTCCTAT GCATTGGCCC CGATCTATGG CAATTTCTGG AGGGGGGGTC TGGCTCAACT CTTTATGCCA AAAAGAAGGC  7786
AAAGCATATT GAGAAAGGCC AAATTCACAT TTCCTACAGC ATAATCTATG CCAGTGGCCC CGTGGGGCTT GGCTTAGAAT TCCCAGGTGC TCTTCCCAGG GAACCATCAG TCTGGACTGA GAGGACCTTC  7916
TCTCTCAGGT GGGACCCGGC CCTGTCCTCC CTGGCAGTGC CGTGTTCTGG GGGTCCTCCT CTCTGGGTCT CACTGCCCCT GGGGTCTCTC CAGCTACCTT TGCTCCATGT TCCTTTGTGG CTCTGGTCTG  8046
TGTCTGGGGT TTCCAGGGGT CTCGGGCTTC CCTGCTGCCC ATTCCTTCTC TGGTCTCACG GCTCCGTGAC TCCTGAAAAC CAACCAGCAT CCTACCCCTT TGGATTGACA CCTGTTGGCC ACTCCTTCTG  8176
GCAGGAAAAG TCACCGTTGA TAGGGTTCCA CGGCATAGAC AGGTGGCTCC GCGCCAGTGC CTGGGACGTG TGGGTGCACA GTCTCCGGGT GAACCTTCTT CAGGCCCTCT CCCAGGCCTG CAGGGGCACA  8306
                                                                                                 224
                                                                                                Gly Glu Tyr Asp Leu Arg Arg Trp Glu Lys Trp Glu Leu Asp
GCAGTGGGTG GGCCTCAGGA AAGTGCCACT GGGGAGAGGC TCCCCGCAGC CCACTCTGAC TGTGCCCTCT GCCCTGCAG GA GAG TAT GAC CTG CGG CGC TGG GAG AAG TGG GAG CTG GAC  8426
                                                                                                                 O
                                                                                                                 ◆
Leu Asp Ile Lys Glu Val Phe Val His Pro Asn Tyr Ser Lys Ser Thr Thr Asp Asn Asp Ile Ala Leu Leu His Leu Ala Gln Pro Ala Thr Leu Ser Gln Thr
CTG GAC ATC AAG GAG GTC TTC GTC CAC CCC AAC TAC AGC AAG AGC ACC ACC GAC AAT GAC ATC GCA CTG CTG CAC CTG GCC CAG CCC GCC ACC CTC TCG CAG ACC  8531
```

FIG. 2C

```
Ile Val Pro Ile Cys Leu Pro Asp Ser Gly Leu Ala Glu Arg Glu Leu Asn Gln Ala Gly Gln Glu Thr Leu Val Thr Gly Trp Gly Tyr His Ser Ser Arg Glu
ATA GTG CCC ATC TGC CTC CCG GAC AGC GGC CTT GCA GAG CGC GAG CTC AAT CAG GCC GGC CAG GAG ACC CTC GTG ACG GGC TGG GGC TAC CAC AGC AGC CGA GAG    8636

Lys Glu Ala Lys Arg Asn Arg Thr Phe Val Leu Asn Phe Ile Lys Ile Pro Val Val Pro His Asn Glu Cys Ser Glu Val Met Ser Asn Met Val Ser Glu Asn
AAG GAG GCC AAG AGA AAC CGC ACC TTC GTC CTC AAC TTC ATC AAG ATT CCC GTG GTC CCG CAC AAT GAG TGC AGC GAG GTC ATG AGC AAC ATG GTG TCT GAG AAC    8741

Met Leu Cys Ala Gly Ile Leu Gly Asp Arg Gln Asp Ala Cys Glu Gly Asp Ser Gly Gly Pro Met Val Ala Ser Phe His Gly Thr Trp Phe Leu Val Gly Leu
ATG CTG TGT GCG GGC ATC CTC GGG GAC CGG CAG GAT GCC TGC GAG GGC GAC AGT GGG GGG CCC ATG GTC GCC TCC TTC CAC GGC ACC TGG TTC CTG GTG GGC CTG    8846

Val Ser Trp Gly Glu Gly Cys Gly Leu Leu His Asn Tyr Gly Val Tyr Thr Lys Val Ser Arg Tyr Leu Asp Trp Ile His Gly His Ile Arg Asp Lys Glu Ala
GTG AGC TGG GGT GAG GGC TGT GGG CTC CTT CAC AAC TAC GGC GTT TAC ACC AAA GTC AGC CGC TAC CTC GAC TGG ATC CAT GGG CAC ATC AGA GAC AAG GAA GCC    8951
                        419
Pro Gln Lys Ser Trp Ala Pro STOP
CCC CAG AAG AGC TGG GCA CCT TAG  CGACCCTCCC TGCAGGGCTG GGCTTTTGCA TGGCAATGGA TGGGACATTA AAGGGACATG TAACAAGCAC ACCGGCCTGC TGTTCTGTCC TTCCATCCCT    9075
CTTTTGGGCT CTTCTGGAGG GAAGTAACAT TTACTGAGCA CCTGTTGTAT GTCACATGCC TTATGAATAG AATCTTAACT CCTAGAGCAA CTCTGTGGGG TGGGGAGGAG CAGATCCAAG TTTTGCGGGG    9205

TCTAAAGCTG TGTGTGTTGA GGGGGATACT CTGTTTATGA AAAAGAATAA AAAACACAAC CACGAAGCCA CTAGAGCCTT TTCCAGGGCT TTGGGAAGAG CCTGTGCAAG CCGGGGATGC TGAAGGTGAG    9335

GCTTGACCAG CTTTCCAGCT AGCCCAGCTA TGAGGTAGAC ATGTTTAGCT CATATCACAG AGGAGGAAAC TGAGGGGTCT GAAAGGTTTA CATGGTGGAG CCAGGATTCA AATCTAGGTC TGACTCCAAA    9465
ACCCAGGTGC TTTTTTCTGT TCTCCACTGT CCTGGAGGAC AGCTGTTTCG ACGGTGCTCA GTGTGGAGGC CACTATTAGC TCTGTAGGGA AGCAGCCAGA GACCCAGAAA GTGTTGGTTC AGCCCAGAAT    9595
```

FIG. 2D

```
                                                                                                  -42     -40                                     -10
                                                                                                  Met Trp Gln Leu Thr Ser Leu Leu Leu Phe Val Ala Thr
CGG CGA ACT TGC AGT ATC TCC ACG ACC CGC CCC TGT GCC AGT GCC TCC AGA ATG TGG CAG CTC ACA AGC CTC CTG CTG TTC GTG GCC ACC    39

                                                  -20                                     -10                                     -1  +1
Trp Gly Ile Ser Gly Thr Pro Ala Pro Leu Asp Ser Val Phe Ser Ser Ser Glu Arg Ala His Gln Val Leu Arg Ile Arg Lys Arg Ala
TGG GGA ATT TCC GGC ACA CCA GCT CCT CTT GAC TCA GTG TTC TCC AGC AGC GAG CGT GCC CAC CAG GTG CTG CGG ATC CGC AAA CGT GCC   129

                                          10                                      20                                      30
Asn Ser Phe Leu Glu Glu Leu Arg His Ser Ser Leu Glu Arg Glu Cys Ile Glu Glu Ile Cys Asp Phe Glu Glu Ala Lys Glu Ile Phe
AAC TCC TTC CTG GAG GAG CTC CGT CAC AGC AGC CTG GAG CGG GAG TGC ATA GAG GAG ATC TGT GAC TTC GAG GAG GCC AAG GAA ATT TTC   219

                                          40                                      50                                      60
Gln Asn Val Asp Asp Thr Leu Ala Phe Trp Ser Lys His Val Asp Gly Asp Gln Cys Leu Val Leu Pro Leu Glu His Pro Cys Ala Ser
CAA AAT GTG GAT GAC ACA CTG GCC TTC TGG TCC AAG CAC GTC GAC GGT GAC CAG TGC TTG GTC TTG CCC TTG GAG CAC CCG TGC GCC AGC   309

                                          70                                      80                                      90
Leu Cys Cys Gly His Gly Thr Cys Ile Asp Gly Ile Gly Ser Phe Ser Cys Asp Cys Arg Ser Gly Trp Glu Gly Arg Phe Cys Gln Arg
CTG TGC TGC GGG CAC GGC ACG TGC ATC GAC GGC ATC GGC AGC TTC AGC TGC GAC TGC CGC AGC GGC TGG GAG GGC CGC TTC TGC CAG CGC   399

                                         100                                     110                                     120
Glu Val Ser Phe Leu Asn Cys Ser Leu Asp Asn Gly Gly Cys Thr His Tyr Cys Leu Glu Glu Val Gly Trp Arg Arg Cys Ser Cys Ala
GAG GTG AGC TTC CTC AAT TGC TCT CTG GAC AAC GGC GGC TGC ACG CAT TAC TGC CTA GAG GAG GTG GGC TGG CGG CGC TGT AGC TGT GCG   489

                                         130                                     140                                     150
Pro Gly Tyr Lys Leu Gly Asp Asp Leu Leu Gln Cys His Pro Ala Val Lys Phe Pro Cys Gly Arg Pro Trp Lys Arg Met Glu Lys Lys
CCT GGC TAC AAG CTG GGG GAC GAC CTC CTG CAG TGT CAC CCC GCA GTG AAG TTC CCT TGT GGG AGG CCC TGG AAG CGG ATG GAG AAG AAG   579

                                         160                                     170                                     180
Arg Ser His Leu Lys Arg Asp Thr Glu Asp Gln Glu Asp Gln Val Asp Pro Arg Leu Ile Asp Gly Lys Met Thr Arg Arg Gly Asp Ser
CGC AGT CAC CTG AAA CGA GAC ACA GAA GAC CAA GAA GAC CAA GTA GAT CCG CGG CTC ATT GAT GGG AAG ATG ACC AGG CGG GGA GAC AGC   669
```

FIG. 3A 190 200 210
Pro Trp Gln Val Val Leu Leu Asp Ser Lys Lys Lys Leu Ala Cys Gly Ala Val Leu Ile His Pro Ser Trp Val Leu Thr Ala Ala His
CCC TGG CAG GTG GTC CTG CTC GAC TCA AAG AAG AAG CTG GCC TGC GGG GCA GTG CTC ATC CAC CCC TCC TGG GTG CTG ACA GCG GCC CAC 759

220 230 240
Cys Met Asp Glu Ser Lys Lys Leu Leu Val Arg Leu Gly Glu Tyr Asp Leu Arg Arg Trp Glu Lys Trp Glu Leu Asp Leu Asp Ile Lys
TGC ATG GAC GAG TCC AAG AAG CTC CTT GTC AGG CTT GGA GAG TAT GAC CTG CGG CGC TGG GAG AAG TGG GAG CTG GAC CTG GAC ATC AAG 849

◆ 250 260 270
Glu Val Phe Val His Pro Asn Tyr Ser Lys Ser Thr Thr Asp Asn Asp Ile Ala Leu Leu His Leu Ala Gln Pro Ala Thr Leu Ser Gln
GAG GTC TTC GTC CAC CCC AAC TAC AGC AAG AGC ACC ACC GAC AAT GAC ATC GCA CTG CTG CAC CTG GCC CAG CCC GCC ACC CTC TCG CAG 939

280 290 300
Thr Ile Val Pro Ile Cys Leu Pro Asp Ser Gly Leu Ala Glu Arg Glu Leu Asn Gln Ala Gly Gln Glu Thr Leu Val Thr Gly Trp Gly
ACC ATA GTG CCC ATC TGC CTC CCG GAC AGC GGC CTT GCA GAG CGC GAG CTC AAT CAG GCC GGC CAG GAG ACC CTC GTG ACG GGC TGG GGC 1029

310 ◆ 320 ◆ 330
Tyr His Ser Ser Arg Glu Lys Glu Ala Lys Arg Asn Arg Thr Phe Val Leu Asn Phe Ile Lys Ile Pro Val Val Pro His Asn Glu Cys
TAC CAC AGC AGC CGA GAG AAG GAG GCC AAG AGA AAC CGC ACC TTC GTC CTC AAC TTC ATC AAG ATT CCC GTG GTC CCG CAC AAT GAG TGC 1119

340 350 360
Ser Glu Val Met Ser Asn Met Val Ser Glu Asn Met Leu Cys Ala Gly Ile Leu Gly Asp Arg Gln Asp Ala Cys Glu Gly Asp Ser Gly
AGC GAG GTC ATG AGC AAC ATG GTG TCT GAG AAC ATG CTG TGT GCG GGC ATC CTC GGG GAC CGG CAG GAT GCC TGC GAG GGC GAC AGT GGG 1209

370 380 390
Gly Pro Met Val Ala Ser Phe His Gly Thr Trp Phe Leu Val Gly Leu Val Ser Trp Gly Glu Gly Cys Gly Leu Leu His Asn Tyr Gly
GGG CCC ATG GTC GCC TCC TTC CAC GGC ACC TGG TTC CTG GTG GGC CTG GTG AGC TGG GGT GAG GGC TGT GGG CTC CTT CAC AAC TAC GGC 1299

400 410 419
Val Tyr Thr Lys Val Ser Arg Tyr Leu Asp Trp Ile His Gly His Ile Arg Asp Lys Glu Ala Pro Gln Lys Ser Trp Ala Pro STOP
GTT TAC ACC AAA GTC AGC CGC TAC CTC GAC TGG ATC CAT GGG CAC ATC AGA GAC AAG GAA GCC CCC CAG AAG AGC TGG GCA CCT TAG CGA 1389

FIG. 3B

CCC TCC CTG CAG GGC TGG GCT TTT GCA TGG CAA TGG ATG GCA CAT TAA ACG GAC ATG TAA CAA GCA CAC CGG CCT GCT GTT CTG TCC TTC 1479

CAT CCC TCT TTT GGG CTC TTC TGG AGG GAA GTA ACA TTT ACT GAG CAC CTG TTG TAT GTC ACA TGC CTT ATG AAT AGA ATC TTA ACT CCT 1569

AGA GCA ACT CTG TGG GGT GGG GAG GAG CAG ATC CAA GTT TTG CGG GGT CTA AAG CTG TCT GTC TTG AGG GGG ATA CTC TGT TTA TGA AAA 1659

AGA ATA AAA AAC ACA ACC ACG AAA AAA AAA $_{3'}$ 1689

FIG. 3C

DNA SEQUENCE CODING FOR PROTEIN C

Matter enclosed in heavy brackets [ ] appears in the original patent but forms no part of this reissue specification; matter printed in italics indicates the additions made by reissue.

GOVERNMENT SUPPORT

This invention was made with government support under National Institutes of Health grant number HL16919. The government has certain rights in the invention.

TECHNICAL FIELD

The present invention relates to sequences coding for plasma proteins in general and, more specifically, to a DNA sequences which codes for a protein having substantially the same structure and/or activity of human protein C.

BACKGROUND ART

Protein C is a zymogen, or precursor, of a serine protease which plays an important role in the regulation of blood coagulation and generation of fibrinolytic activity in vivo. It is synthesized in the liver as a single-chain polypeptide which undergoes considerable processing to give rise to a two-chain molecule comprising heavy (Mr=40,000) and light (Mr=21,000) chains held together by disulphide bonds. The circulating two-chain intermediate is converted to the biologically active form of the molecule, known as "activated protein C" (APC), by the thrombin-mediated cleavage of a 12-residue peptide from the amino-terminus of the heavy chain. The cleavage reaction is augmented in vivo by thrombomodulin, an endothelia cell cofactor (Esmon and Owen, Proc. Natl. Acad. Sci. USA 78: 2249–2252, 1981).

Protein C is a vitamin K-dependent glycoprotein which contains approximately eleven residues of gammacarboxyglutamic acid (gla) and one equivalent of betahydroxyaspartic acid which are formed by post-translational modifications of glutamic acid and aspartic acid residues, respectively. The post-translational formation of specific gamma-carboxyglutamic acid residues in protein C requires vitamin K. These unusual amino acid residues bind to calcium ions and are believed to be responsible for the interaction of the protein with phospholipid, which is required for the anticoagulant activity of protein C.

In contrast to the coagulation-promoting action of other vitamin K-dependent plasma proteins, such as factor VII, factor IX, and factor X, activated protein C acts as regulator of the coagulation process through the inactivation of factor Va and factor VIIa by limited proteolysis. The inactivation of factors Va and VIIIa by protein C is dependent upon the presence of acidic phospholipids and calcium ions. Protein S has been reported to regulate this activity by accelerating the APC-catalyzed proteolysis of factor Va (Walker, J. Biol. Chem. 255:5521–5524, 1980).

Protein C has also been implicated in the action of plasminogen activator (Kisiel and Fujikawa, Behring Inst. Mitt. 73:29–42, 1983). Infusion of bovine APC into dogs results in increased plasminogen activator activity (Comp and Esmon, J. Clin. Invest. 68: 1221–1228, 1981). Recent studies (Sakata et al., Proc. Natl. Acad, Sci. USA 82: 1121–1125, 1985) have shown that addition of APC to cultured endothelia cells leads to a rapid, dose-dependent increase in fibrinolytic activity in the conditioned media, reflecting increases in the activity in both urokinase-related and tissue-type plasminogen activators by the cells. APC treatment also results in a dose-dependent decrease in anti-activator activity.

Inherited protein C deficiency is associated with recurrent thrombotic disease (Broekmans et al., New Eng. J. Med. 309: 340–344, 1983; and Seligsohn et al., New Eng. J. Med. 310: 559–562, 1984) and may result from genetic disorder or from trauma, such as liver disease or surgery. This condition is generally treated with oral anti-coagulants. Beneficial effects have also been obtained through the infusion of protein C-containing normal plasma (see Gardiner and Griffin in Prog. in Hematology,ed. Brown, Grune & Stratton, NY, 13: 265–278). In addition, some investigation have discovered that the anti-coagulant activity of protein C is useful in treating thrombotic disorders, such as venous thrombosis (WO 85/00521). In some parts of the world, it is estimated that approximately 1 in 16,000 individuals exhibit protein C deficiency. Further, a total deficiency in protein C is fatal in newborns.

While natural protein C may be purified from clotting factor concentrates (Marlar et al., Blood 59: 1067–1072) or from plasma (Kisiel, ibid), it is a complex and expensive process, in part due to the limited availability of the starting material and the low concentration of protein C in plasma. Furthermore, the therapeutic use of products derived from human blood carries the risk of disease transmission by, for example, hepatitis virus, cytomegalovirus, or the causative agent of acquired immune deficiency syndrome (AIDS). In view of protein C's clinical applicability in the treatment of thrombotic disorders, the production of useful quantities of protein C and activated protein C is clearly invaluable.

DISCLOSURE OF INVENTION

Briefly stated, the present invention discloses a DNA sequence which codes for a protein having substantially the same biological activity as human protein C.

In addition, the present invention discloses a recombinant plasmid or bacteriophage transfer vector comprising a cDNA sequence comprising the protein C gene cDNA sequence. The amino acid and DNA sequences of this cDNA coding for human protein C are also disclosed.

Other aspects of the invention will become evident upon reference to the detailed description and attached drawings.

BRIEF DESCRIPTION OF THE DRAWINGS

FIG. 2 illustrates the complete genomic sequence, including exons and introns for human protein C. Arrowheads indicate intron-exon splice junctions. The polyadenylation or processing sequences of A-T-T-A-A-A and A-A-T-A-A-A at the 3' end are boxed. ♦, potential carbohydrate binding sites; ↙, apparent cleavage sites for processing of the connecting dipeptide; ↓, site of cleavage in the heavy chain when protein C is converted to activated protein C; ●, sites of polyadenylation.

FIG. 3 depicts the amino acid and DNA sequences for a cDNA coding for human protein C.

BEST MODE FOR CARRYING OUT THE INVENTION

Figure 1:
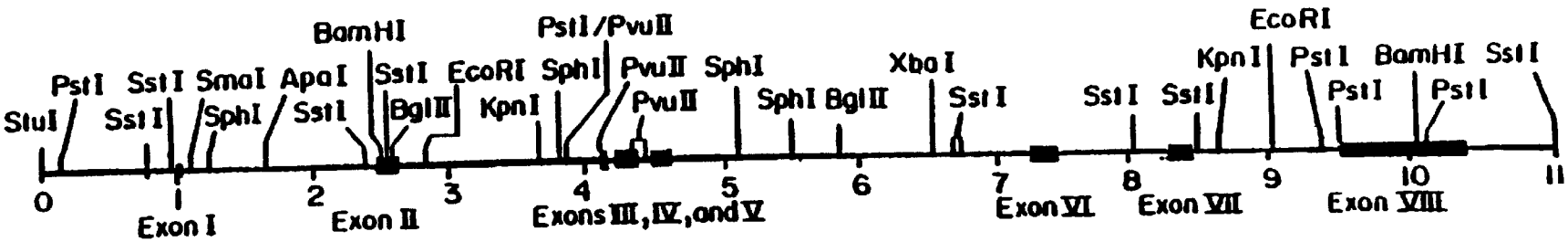
FIG. 1 illustrates a restriction enzyme map of the genomic DNA coding for human protein C.

Prior to setting forth the invention, it may be helpful to an understanding thereof to set forth definitions of certain terms to be used hereinafter.

Biological Activity: A function or set of functions performed by a molecule in a biological context (i.e., in an organism or an in vitro facsimile). Biological activities of proteins may be divided into catalytic and effector activities. Catalytic activities of the vitamin K-dependent plasma proteins generally involve the specific proteolytic cleavage of other plasma proteins, resulting in activation or deactivation of the substrate. Effector activities include specific binding of the biologically active molecule to calcium or other small molecules, to macromolecules, such as proteins, or to cells. Effector activity frequently augments, or is essential to, catalytic activity under physiological conditions.

For protein C, biological activity is characterized by its anticoagulant and fibrinolytic properties. Protein C, when activated, inactivities factor Va and factor VIIIa in the presence of phospholipid and calcium. Protein S appears to be involved in the regulation of this function (Walker, ibid). Activated protein C also enhances fibronolysis, an effect believed to be mediated by the lowering of levels of plasminogen activator inhibitors (van Hinsbergh et al., Blood 65: 444–451, 1985). As more fully described below, Exons VII and VIII are primarily responsible for the catalytic activity of protein C.

Transfer Vector: A DNA molecule which contains, inter alia, genetic information which ensures its own replication when transferred to a host microorganism strain. Examples of transfer vectors commonly used for recombinant DNA are plasmids and certain bacteriophages. Transfer vectors normally include an origin of replication and sequences necessary for efficient transcription and translation of DNA.

As noted above, protein C is synthesized as a single-chain polypeptide which undergoes considerable processing to give rise to a two-chain molecule; a heavy chain ($M_r$ 41,000) and a light chain ($M_r$ 12,000), held together by a disulfide bond.

Within the present invention, a λgtll cDNA library was prepared from human liver mRNA. This library was then screened with $125_I$ labeled antibody to human protein C. Antibody-reactive clones were further analyzed for the synthesis of a fusion protein of B-galactosidase and protein C in the λgtll vector.

One of the clones gave a strong signal with the antibody probe and was found to contain an insert of approximately 1400 bp. DNA sequence analysis of the DNA insert revealed a predicted amino acid sequence which shows a high degree of homology to major portions of the bovine protein C, as determined by Fernlund and Stenflo (J. Biol. Chem. 257: 12170–12179; J. Biol. Chem. 257: 12180–12190). Chem. 257: 12170

The DNA insert contained the majority of the coding region for protein C beginning with amino acid 65 of the light chain, including the entire heavy chain coding region, and proceeding to the termination codon. Further, following the stop codon of the heavy chain, there are 294 base pairs of 3' noncoding sequence and a poly (A) tail of 9 base pairs. The processing or polyadenylation signal A-A-T-A-A-A was present 13 base pairs upstream from the poly (A) tail in this cDNA insert. This sequence is one of two potential polyadenylation sites.

The cDNA sequence also contains the dipeptide LysArg at position 156–157, which separates the light chain from the heavy chain and is removed during processing by proteolytic cleavage. Upon activation by thrombin, the heavy chain of human protein C is cleaved between arginine-12 and leucine-13, releasing the activation peptide.

In order to obtain the remainder of the light chain coding sequence (amino acids 1–64), a human genomic library in λ Charon 4A phage was screened for genomic clones of human protein C using the cDNA described above as a hybridization probe. Three different λ Charon 4A phage were isolated that contained overlapping inserts for the gene coding for protein C.

The position of exons on the three phage clones were determined by Southern blot hybridization of digests of these clones with probes made from the 1400 bp cDNA described above. The genomic DNA inserts in these clones were mapped by single and double restriction enzyme digestion followed by agarose gel electrophoresis, Southern blotting, and hybridization to radiolabeled 5' and 3' probes derived from the cDNA for human protein C, as shown in FIG. 1.

DNA sequencing studies were performed using the dideoxy chain-termination method. As shown in FIG. 2, the nucleotide sequence for the gene for human protein C spans approximately 11 kb of DNA. These studies further revealed a potential pre-pro leader sequence of 42 amino acids. Based on homology with the leader sequence of bovine protein C in the region −1 to −20, it is likely that the pre-pro leader sequence is cleaved by a signal peptidase following the Ala residue at position −10. Processing to the mature protein involves additional proteolytic cleavage following residue −1 to remove the amino-terminal propeptide, and at residues 155 and 157 to remove the Lys-Arg dipeptide which connects the light and heavy chains. This final processing yields a light chain of 155 amino acids and a heavy chain of 262 amino acids.

As noted above, the protein C gene is composed of eight exons ranging in size from 25 to 885 nucleotides, and seven introns ranging in size from 92 to 2668 nucleotides. Exon I and a portion of Exon II code for the 42 amino acid pre-pro peptide. The remaining portion of Exon II, Exon III, Exon IV, Exon V, and a portion of Exon VI code for the light chain of protein C. The remaining portion of Exon VI, Exon VII, and Exon VIII code for the heavy chain of protein C. The amino acid and DNA sequences for a cDNA coding for human protein C are shown in FIG. 3.

The location of the introns in the gene for protein C are primarily between various functional domains. Exon II spans the highly conserved region of the leader sequence and the gamma-carboxyglutamic acid (gla) domain. Exon III includes a stretch of eight amino acids which connect the Gla and growth factor domains. Exons IV and V each represent a potential growth factor domain, while Exon VI covers a connecting region which includes the activation peptide. Exons VII and VIII cover the catalytic domain typical of all serine proteases.

Figure 4:
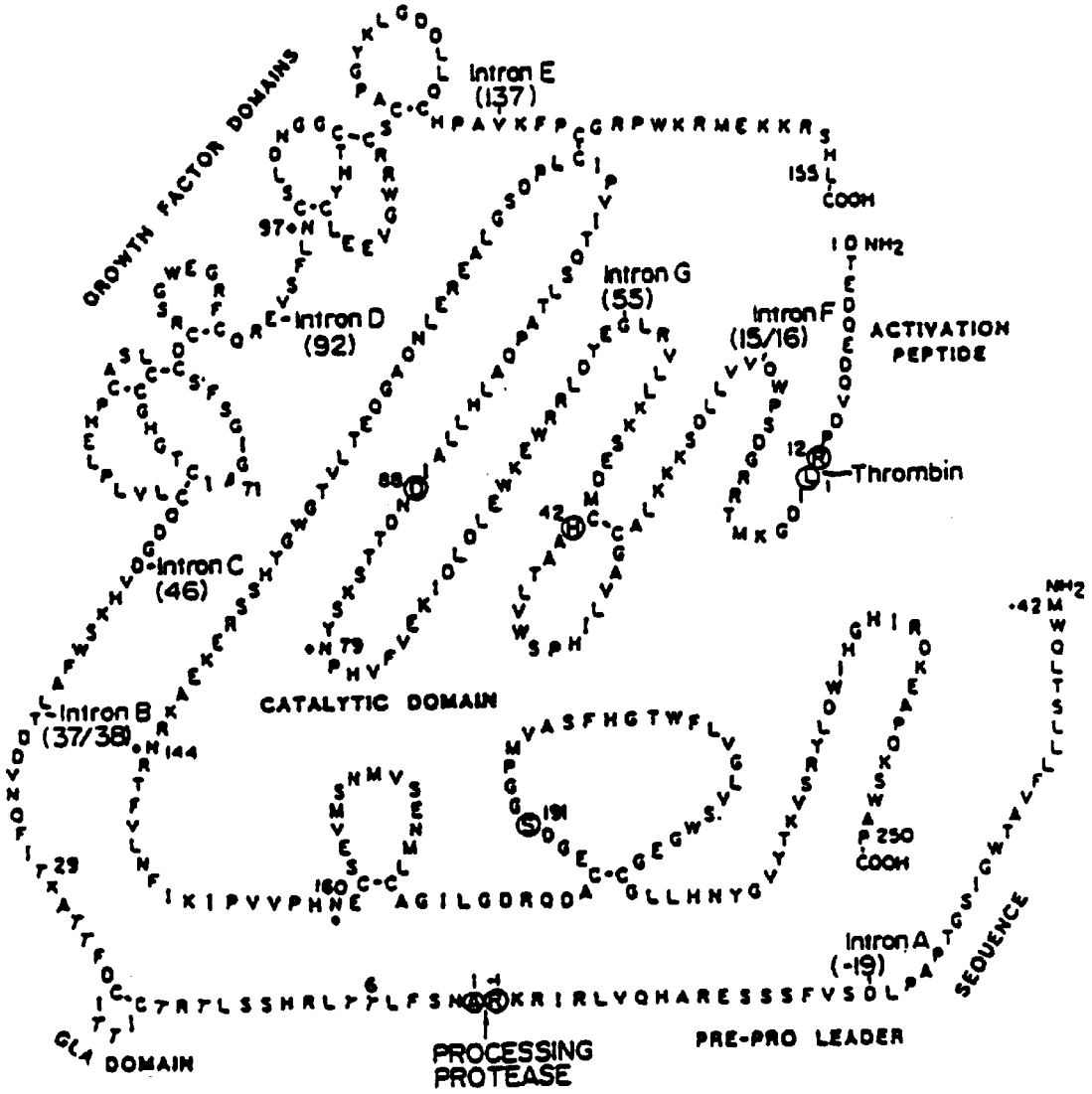
FIG. 4 illustrates a proposed model for the structure of human protein C.

The amino acid sequence and tentative structure for human pre-pro protein C are shown in FIG. 4. Protein C is shown without the Lys-Arg dipeptide, which connects the light and heavy chains. The location of the seven introns (A through G) is indicated by solid bars. Amino acids flanking known proteolytic cleavage sites are circled. ♦ designates potential carbohydrate binding sites. The first amino acid in the light chain, activation peptide, and heavy chain start with number 1, and differ from the shown in FIGS. 2 and 3.

Carbohydrate attachment sites are located at residue 97 in the light chain and residues 79, 144, and 160 in the heavy chain, according to the numbering scheme of FIG. 4. The carbohydrate moiety is covalently linked to Asn, but Thr, Ser, or Gln may be substituted. In the majority of instances, the carbohydrate attachment environment can be represented by N-X-Ser or N-X-Thr, where N=Asn, Thr, Ser, or Gln, and X=any amino acid.

The catalytic domain of protein C, which is encoded by Exons VII and VIII, plays a regulatory role in the coagulation process. This domain possesses serine protease activity which specifically cleaves certain plasma proteins (i.e., factors Va and VIIIa), resulting in their activation or deactivation. As a result of this selective proteolysis, protein C displays anticoagulant and fibronolytic activities.

The example which follows describes the cloning of DNA sequences encoding human protein C.

EXAMPLE

Restriction endonucleases and other DNA modification enzymes (e.g., $T_4$ polynucleotide kinase, bacterial alkaline phosphatase, Klenow DNA polymerase, $T_4$ polynucleotide ligase) may be obtained from Bethesda Research Laboratories (BRL) and New England Biolabs and are used as directed by the manufacturer, unless otherwise noted.

CLONING OF DNA SEQUENCES ENCODING HUMAN PROTEIN C

A cDNA coding for a portion of human was prepared as described by Foster and Davie (PNAS (USA) 81: 4766–4770, 1984, herein incorporated by reference). Briefly, a λgtll cDNA library was prepared from human liver mRNA by conventional methods. Clones were screened using $125_I$-labeled affinity-purified antibody to human protein C, and phage were prepared from positive clones by the plate lysate method (Maniatis et al., ibid), followed by banding on a cesium chloride gradient. The cDNA inserts were removed using Eco RI and subcloned into plasmid pUC9 (Vieira and Messing, Gene 19: 259–268, 1982). Restriction fragments were subcloned in the phage vectors M13mp10 and m13mpll (Messing, Meth. in Enzymology 101: 20–77, 1983) and sequenced by the dideoxy method (Sanger et al., Proc. Natl. Acad. Sci. USA 74: 5463–5467, 1977). A clone was selected which contained DNA corresponding to the known sequence of human protein C (Kisiel, ibid) and encoded protein C beginning at amino acid 65 of the light chain and extending through the heavy chain and into the 3' non-coding region. This clone was designated λHC1375.

The cDNA insert from λHC1375 was nick translated using $\alpha$–$^{32}$P dNTP's and used to probe a human genomic library in phage λ Charon 4A (Maniatis et al., Cell 15: 687–702, 1978) using the plaque hybridization procedure of Benton and Davis (Science 196: 181–182, 1977) as modified by Woo (Meth. in Enzymology 68: 381–395, 1979). Positive clones were isolated and plaque-purified (by Foster et al., *PNAS* (USA) 82: 4673–4677, 1985, herein incorporated by reference).

Phage DNA was prepared from positive clones by the method of Silhavy et al. (Experiments with Gene Fusion, Cold Spring Harbor Laboratory, 1984). The purified phage DNA was digested with EcoRI and subcloned into pUC9 for further mapping and sequencing studies. Further analysis suggested that the gene for protein C was present in three EcoRI fragments. In order to generate overlapping protein C DNA sequences, purified phage DNA was digested with Bgl II and subcloned into pUC9.

The sequences of the EcoRI and Bgl II protein C fragments were determined by subcloning the fragments into M13 phage cloning vectors. Sequence analysis of the overlapping fragments established the DNA sequence of the entire protein C gene.

Alternatively, the complete DNA sequence has been determined using a second cDNA clone isolated from a λgtll cDNA library. This clone encodes a major portion of protein C, beginning at amino acid 24 and including the heavy chain coding region, termination codon, and 3' noncoding region. The insert from this λ phage clone was subcloned into pUC9 and the resultant plasmid designated pHC 6L.

This pHC 6L insert was nick translated and used to probe a human genomic library in phage λ Charon 4A. One genomic clone was identified which contained a 4.4 kb EcoRI fragment corresponding to the 5' end of the protein C gene. This phage clone was subcloned into pUC9 and the resultant plasmid designated pHCR 4.4. DNA sequence analysis revealed that the pHCR 4.4 insert comprised two exons, encoding amino acids −42 to −19, and amino acids −19 to 37. Thus, the DNA sequence of the entire protein C gene was established due to the overlapping sequences of pHC 6L (24 to 3' noncoding region) and pHCR 4.4 (−42 to 37).

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated human DNA sequence which codes for a protein having substantially the same biological activity as human protein C, *wherein said protein comprises a light chain as shown in FIG. 3 from amino acid number 1 to amino acid number 155, and a heavy chain as shown in FIG. 3 from amino acid number 158 to amino acid number 419.*

2. An isolated DNA sequence comprising the sequence of FIG. 2, from bp 1 to bp 8972, which sequence codes for human protein C.

3. A bacterial plasmid or bacteriophage transfer vector comprising a cDNA sequence comprising the human protein C gene cDNA sequence.

* * * * *

UNITED STATES PATENT AND TRADEMARK OFFICE

CERTIFICATE OF CORRECTION

PATENT NO. : RE 37,958 E
DATED : February 10, 2003
INVENTOR(S) : Foster et al.

It is certified that error appears in the above-identified patent and that said Letters Patent is hereby corrected as shown below:

Column 1,
Line 12, insert the following section:

-- CROSS-REFERENCE TO RELATED APPLICATION

A continuation application of this reissue patent has been filed as U.S. Patent Application Serial No. 10/217,105, filed 8-13-02. --

Line 17, change “sequences” to -- sequence --.
Lines 34 and 64, change “endothelia” to -- endothelial --.
Line 65, change “in” (second occurrence) to -- of --.

Column 2,
Line 11, change “Hematology,ed.” to -- Hematology, ed. --
Lines 12-13, change “investigation” to -- investigators --.

Column 3,
Line 15, change “inactivities” to -- inactivates --
Line 18, change “fibronolysis,” to -- fibrinolysis, --.

Column 5,
Line 7, change “fibronolytic” to -- fibrinolytic --.

Signed and Sealed this

Twenty-fifth Day of March, 2003

JAMES E. ROGAN
*Director of the United States Patent and Trademark Office*